(12) United States Patent
Fachini

(10) Patent No.: US 7,662,848 B2
(45) Date of Patent: Feb. 16, 2010

(54) PROCESS FOR THE PREPARATION OF FLUVASTATIN SODIUM SALT

(75) Inventor: Marco Fachini, Padua (IT)

(73) Assignee: F.I.S. Fabbrica Italiana Sintetici S.p.A., Alte Di Montecchio Maggiore (Vicenza) (IT)

( * ) Notice: Subject to any disclaimer, the term of this patent is extended or adjusted under 35 U.S.C. 154(b) by 32 days.

(21) Appl. No.: 11/785,702

(22) Filed: Apr. 19, 2007

(65) Prior Publication Data
US 2007/0249704 A1  Oct. 25, 2007

(30) Foreign Application Priority Data
Apr. 20, 2006  (EP) .................................. 06112856

(51) Int. Cl.
*A61K 31/404*  (2006.01)
(52) U.S. Cl. ...................................... 514/419
(58) Field of Classification Search .................. 514/419
See application file for complete search history.

(56) References Cited

U.S. PATENT DOCUMENTS 4,739,073 A    4/1988  Kathawala
2005/0159615 A1*  7/2005  Lifshitz-Liron et al. ..... 560/179

FOREIGN PATENT DOCUMENTS

| EP | 0 363 934 | 4/1990 |
| WO | WO 01/92223 | 12/2001 |
| WO | WO 2004/113292 | 12/2004 |

\* cited by examiner

*Primary Examiner*—Rebecca L Anderson
*Assistant Examiner*—Shawquia Young
(74) *Attorney, Agent, or Firm*—Dickstein Shapiro LLP

(57) ABSTRACT

The present invention is directed to a process for preparing Fluvastatin Sodium salt by basic hydrolysis of its alkyl ester. The reaction is performed in conditions suitable to allow a selective hydrolysis of the desired syn isomer, while the unwanted anti isomer is removed by extraction, thus reducing its content in the final product; this diastereomer is the main impurity of Fluvastatin sodium salt and its ester precursor.

18 Claims, No Drawings

PROCESS FOR THE PREPARATION OF FLUVASTATIN SODIUM SALT

FIELD OF THE INVENTION

The present invention is directed to an improved process for preparing Fluvastatin Sodium salt by basic hydrolysis of its alkyl esters.

BACKGROUND ART

Fluvastatin Sodium salt of formula I (relative stereochemistry) is marketed by Novartis under the trade name of Lescol and belongs to a class of anti-hyperlipidemic agents called statins. Such compounds are HMG-COA reductase inhibitors, i.e. inhibit the enzyme that reduces 3-hydroxy-3-methylglutaric acid to mevalonic acid, thus blocking the biosynthesis of cholesterol and lowering its level in the bloodstream. Most statins resemble mevalonic acid in the sense that they contain the 3,5-dihydroxy carboxylate function, fooling the enzyme to binding to the drug and therefore inhibiting it.

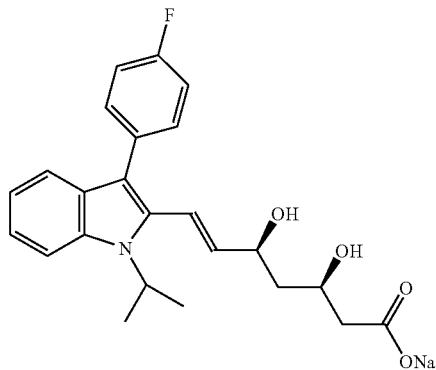

The product patent for Fluvastatin is EP 114027, in which several synthetic routes are described. The last 2 steps (reduction followed by saponification) of the preferred process are better described in the process patent EP 363934, in which the synthesis set forth in Scheme 1 (relative stereochemistry) is described; the drug substance is then obtained by lyophilization of its aqueous solution.

Scheme 1

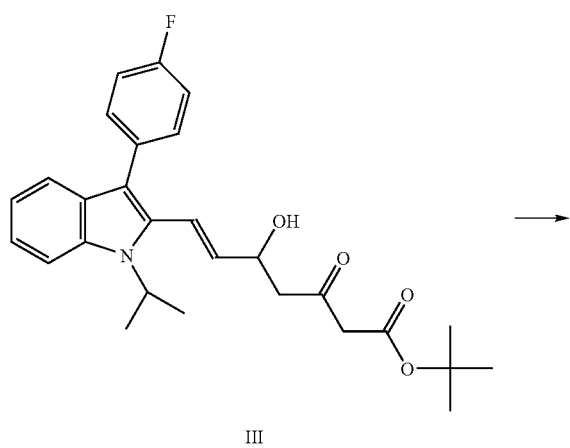

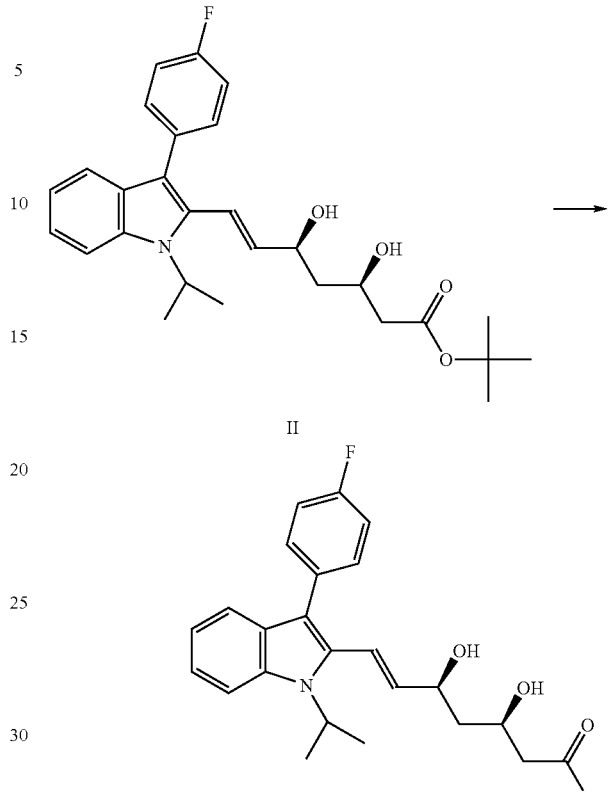

This patent claims a specific order of addition of the reactants in the stereoselective reduction from III to II, in order to achieve a high level of syn stereoselectivity and minimize the unwanted diastereomer, the so called anti isomer IV (relative stereochemistry).

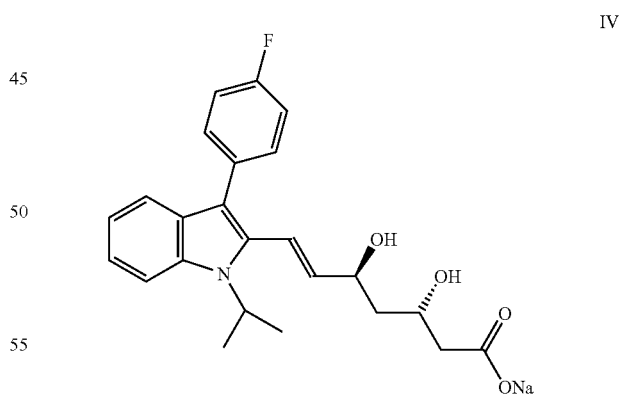

This is well explained in the paper written by Novartis' process research and development group "The Story of Lescol: From Research to Production", *Org. Process Res. Dev.* 2001, 5, 519-527: in the introduction they report that the most difficult challenge was "to form the 3,5-diol exclusively in the syn configuration". This unwanted anti diastereomer is actually the main impurity of Fluvastatin Sodium salt and its ester precursors, as confirmed by the United States Pharmacopoeia monograph of Fluvastatin (*Official Monographs,*

USP 28, First Supplement, USP-NF, 3234), which sets a limit of 0.8% (HPLC) for this impurity and a much lower limit of 0.1% for any other impurity. This high limit set by the USP, which is unusual for impurities in active pharmaceutical ingredients, must be due to the limited stability of Fluvastatin in stressed degradation studies; such limited stability is reported on page 9 of EP 907639, which uses the same HPLC method later adopted by the USP; clearly the anti isomer must be one of the main degradation products and this fact has been actually confirmed by our independent investigations. In conclusion, the content of anti isomer in the active pharmaceutical ingredient must be far below the above set limit to allow for the unavoidable degradation that takes place during storage (showed by the stability studies), i.e. the content of anti isomer must reasonably be below 0.4% and preferably below 0.2%.

Novartis apparently solved the problem of the purification of Fluvastatin Sodium from its anti isomer improving the stereoselectivity of the reduction of the carbonyl to the hydroxyl group, as claimed in EP 363934, affording an ester precursor of better quality. In "The Story of Lescol" is stated on page 526 that starting from the t-butyl ester (which is preferred over the methyl ester, since avoids a lactonization side process that causes isomerization to the anti isomer) such reduction affords a 99:1 selectivity, i.e. we must understand that the ester precursor contains about 1% of the unwanted anti isomer; this means that the ester precursor has to be recrystallized at least twice in order to achieve a reasonable degree of purity, with considerable yield loss. As a matter of fact, the authors of the paper carry on stating that: "only minimal purification occurs in the last step. The saponification leaves Fluvastatin Sodium salt in the aqueous layer, which is freeze-dried, to obtain the drug substance as a white powder".

As shown above, there is still need of an improved process for the preparation of Fluvastatin Sodium salt that allows minimizing the content of anti isomer, without resorting to several crystallizations of its t-butyl ester precursor, which cause considerable yield loss.

SUMMARY OF THE INVENTION

We have surprisingly found that carrying out the saponification step in a suitable aqueous alcoholic solution using less than 1.00 molar amount of sodium hydroxide in respect to the ester allows hydrolyzing selectively the syn Fluvastatin alkyl ester, while leaving unhydrolyzed most of the anti isomer. The residual small amount of Fluvastatin alkyl ester (enriched with the unwanted anti isomer) may be removed by extraction with a suitable solvent, such as t-butyl methyl ether. This gives an aqueous alcoholic solution or suspension of Fluvastatin Sodium salt with a very low content of anti isomer.

DETAILED DESCRIPTION OF THE INVENTION

The present invention is directed to a process for the preparation of Fluvastatin Sodium salt I starting from Fluvastatin alkyl ester of formula V by basic hydrolysis with sodium hydroxide.

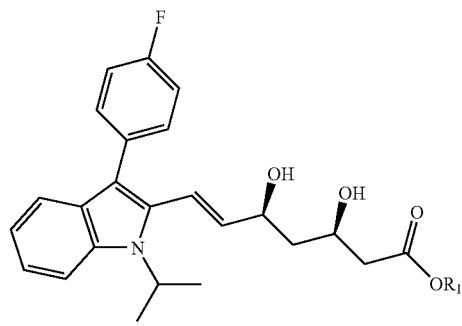

wherein $R_1$ is a $(C_2\text{-}C_6)$ alkyl group.

Preferably, $R_1$ is a branched $(C_3\text{-}C_6)$ alkyl group, more preferably is t-butyl.

We have surprisingly found that carrying out the saponification step in a suitable aqueous alcoholic solution using less than 1.00 molar amount of sodium hydroxide in respect to the ester allows hydrolyzing selectively the syn Fluvastatin alkyl ester V, while leaving unhydrolyzed most of the anti isomer.

Suitable solvents for this reaction are mixtures of a $C_2\text{-}C_8$ aliphatic alcohols, either linear or branched, and water, characterized by a volume ratio between said alcohol and water greater than 5, preferably equal to or greater than 10, most preferably between 20 and 1000. The best volume ratio between the alcohol and water also depends on the nature of the alcohol employed. Preferred alcohols are $C_2\text{-}C_5$ aliphatic alcohols, either linear or branched; most preferred alcohols are ethanol, isopropanol, t-butanol, isobutanol and 2-methyl-2-butanol; even most preferred is t-butanol.

Sodium hydroxide may be added to the reaction mixture as a solid or it may be dissolved in the water used for the reaction and added as a solution. Preferred molar amounts of sodium hydroxide in respect to the ester are from 0.90 to 0.99; most preferred molar amounts are from 0.95 to 0.98.

The saponification reaction may be carried out at a suitable temperature until no increase in the amount of Fluvastatin Sodium salt is detected by a suitable analytical method, such as HPLC. Preferred temperatures for carrying out the reaction are from −10° C. to 50° C.; most preferred temperatures are from 10° C. to 30° C. The time for the reaction to be completed usually ranges from 1 to 8 hours.

The following description refers to suitable work-ups and methods of isolation that can be used at the end of the reaction. Any other suitable method of removing the unhydrolyzed anti isomer may be used.

The solvent may be optionally evaporated under reduced pressure to facilitate the subsequent extraction phase. Water is added to the reaction mixture until the entire solid is dissolved. The solvent may be optionally evaporated under reduced pressure and water added again to facilitate the subsequent extraction phase.

The residual small amount of unhydrolyzed Fluvastatin alkyl ester V (enriched with the unwanted anti isomer) may be removed by extraction with a solvent immiscible with water. Preferred solvents are ethers, esters, ketones, aromatic, aliphatic and chlorinated hydrocarbons; most preferred solvents are t-butyl methyl ether, diethyl ether, diisopropyl ether, methyl ethyl ketone, methyl isobutyl ketone, ethyl acetate, isopropyl acetate, methylene chloride, chloroform and toluene; even most preferred solvent is t-butyl methyl ether. The extraction is repeated until no further removal of the starting material is observed.

The resulting solution of Fluvastatin Sodium salt has a very low content of anti isomer, less than or equal to half of that of the ester starting material, preferably less than or equal to one quarter of that of the ester starting material. Such solution may be concentrated under reduced pressure and then freeze-dried as described in the art.

Fluvastatin Sodium salt may be alternatively isolated by filtration from the reaction mixture at the end of the reaction and is obtained in high yield and purity. In fact the unhydrolyzed Fluvastatin alkyl ester V (enriched with the unwanted anti isomer) is well soluble in the aqueous alcoholic mixture.

Such great reduction of the anti isomer content and the consequent increase in purity of the resulting Fluvastatin Sodium salt is obtained without any substantial yield loss, unlike the traditional methods of subsequent crystallizations of the ester precursor. In fact the only loss of product is practically due the small percentage of unhydrolyzed Fluvastatin alkyl ester V, which depends on the amount of sodium hydroxide used and is preferably less than 10%, most preferably less than 5%. Moreover this small percentage of unhydrolyzed Fluvastatin alkyl ester V contains a large amount of the unwanted anti isomer, usually from 20% to 70%, depending on the initial content and reaction conditions; such amount should have been removed anyway to obtain a product of suitable pharmaceutical purity.

The following examples are set forth to aid in understanding the invention, but are not intended to limit the scope of protection. The reported HPLC purities are referred to syn Fluvastatin alkyl ester V and to syn Fluvastatin Sodium salt, while the anti isomer contents are referred to anti Fluvastatin alkyl ester V and to anti Fluvastatin Sodium salt. The percentage reduction of anti isomer in respect to its initial value in the ester is indicated. The volumes of alcohol and water and the molar amounts of sodium hydroxide in respect to the amount of the ester starting material are also indicated.

EXAMPLES

Example 1

Fluvastatin Sodium salt I

In a round bottom flask are charged 10.0 g (21.4 mmol) of Fluvastatin t-butyl ester (HPLC purity=98.07%, anti isomer=1.24%), 200 mL of ethanol (20 vol.) and a solution of 0.83 g of sodium hydroxide (20.8 mmol, 0.97 eq.) in 4.0 mL of water (0.4 vol.). The mixture is stirred at 20° C. for 5 hours, and then evaporated under reduced pressure. 80 mL of water are added, the solution is evaporated again to a final weight of 43 g, then further 27 mL of water are added. The mixture is extracted with 5×20 mL of t-butyl methyl ether. The resulting aqueous solution (HPLC purity=99.45%, anti isomer=0.31%, 75% reduction) is evaporated at 40° C. under reduced pressure, obtaining 13.5 g of a damp solid.

Example 2

Fluvastatin Sodium salt I

In a round bottom flask are charged 40.0 g (85.5 mmol) of Fluvastatin t-butyl ester (HPLC purity=99.26%, anti somer=0.69%), 400 mL of t-butanol (10 vol.) and a olution of 3.36 g of sodium hydroxide (84.0 mmol, 0.98 q.) in 32 mL of water (0.8 vol.). The mixture is stirred at 21° C. for 6 hours, and then evaporated under reduced pressure. 320 mL of water are added and the solution is evaporated again to a final weight of 335 g. The mixture is extracted with 160 mL of t-butyl methyl ether, then again with 3×80 mL of t-butyl methyl ether. The resulting aqueous solution (HPLC purity=99.68%, anti isomer=0.16%, 77% reduction) may be concentrated and freeze-dried as known in the art.

Example 3

Fluvastatin Sodium salt I

In a round bottom flask are charged 10.0 g (21.4 mmol) of Fluvastatin t-butyl ester (HPLC purity=99.14%, anti isomer=0.81%), 100 mL of isopropanol (10 vol.) and a solution of 0.84 g of sodium hydroxide (21.0 mmol, 0.98 eq.) in 8.0 mL of water (0.8 vol.). The mixture is stirred at 20° C. for 3 hours, and then evaporated under reduced pressure. 80 mL of water are added and the solution is evaporated again to a final weight of 80 g. The mixture is extracted with 40 mL of t-butyl methyl ether, then again with 3×20 mL of t-butyl methyl ether. The resulting aqueous solution is evaporated at 25° C. under reduced pressure, obtaining a slurry (HPLC purity=99.57%, anti isomer=0.24%, 70% reduction), which may be freeze-dried as known in the art.

Example 4

Fluvastatin Sodium salt I

In a round bottom flask are charged 8.0 g (17.1 mmol) of Fluvastatin t-butyl ester (HPLC purity=99.14%, anti isomer=0.81%), 80 mL of isobutanol (10 vol.) and a solution of 0.67 g of sodium hydroxide (16.8 mmol, 0.98 eq.) in 6.4 mL of water (0.8 vol.). The mixture is stirred at 20° C. for 4 hours, and then evaporated under reduced pressure. 64 mL of water are added and the solution is evaporated again to a final weight of 61 g. The mixture is extracted with 32 mL of t-butyl methyl ether, then again with 3×16 mL of t-butyl methyl ether. The resulting aqueous solution is evaporated at 25° C. under reduced pressure, obtaining a slurry (HPLC purity=99.63%, anti isomer=0.28%, 65% reduction), which may be freeze-dried as known in the art.

Example 5

Fluvastatin Sodium salt I

In a round bottom flask are charged 8.6 g (18.3 mmol) of Fluvastatin t-butyl ester (HPLC purity=96.81%, anti isomer=1.71%), 86 mL of t-butanol (10 vol.) and a solution of 0.72 g of sodium hydroxide (18.0 mmol, 0.98 eq.) in 6.9 mL of water (0.8 vol.). The mixture is stirred at 20° C. for 6 hours, and then evaporated under reduced pressure. 60 mL of water are added and the solution is evaporated again to a final weight of 68 g. The mixture is extracted with 34 mL of t-butyl methyl ether, then again with 3×17 mL of t-butyl methyl ether. The resulting aqueous solution is evaporated at 25° C. under reduced pressure, obtaining a slurry (HPLC purity=99.57%, anti isomer=0.30%, 82% reduction), which may be freeze-dried as known in the art.

Example 6

Fluvastatin Sodium salt I

In a round bottom flask are charged 10.0 g (21.4 mmol) of Fluvastatin t-butyl ester (HPLC purity=99.26%, anti isomer=0.69%), 100 mL of 2-methyl-2-butanol (10 vol.) and a solution of 0.84 g of sodium hydroxide (21.0 mmol, 0.98 eq.) in 8.0 mL of water (0.8 vol.). The mixture is stirred at 20° C. for 6 hours, and then evaporated under reduced pressure. 80 mL of water are added and the solution is evaporated again to a final weight of 82 g. The mixture is extracted with 40 mL of t-butyl methyl ether, then again with 3-20 mL of t-butyl methyl ether. The resulting aqueous solution is evaporated at 25° C. under reduced pressure, obtaining a slurry (HPLC purity=99.76%, anti isomer=0.18%, 74% reduction), which may be freeze-dried as known in the art.

Example 7

Fluvastatin Sodium salt I

In a round bottom flask are charged 10.0 g (21.4 mmol) of Fluvastatin t-butyl ester (HPLC purity=98.30%, anti isomer=0.84%), 100 mL of t-butanol (10 vol.) and a solution of 0.84 g of sodium hydroxide (21.0 mmol, 0.98 eq.) in 8.0 mL of water (0.8 vol.). The mixture is stirred at 21° C. for 6 hours. The resulting slurry is filtered, washed with the same solvent mixture and dried overnight at 30° C. in the oven, obtaining 8.92 g of solid (20.6 mmol, 96%; HPLC purity=99.58%, anti isomer=0.15%, 82% reduction).

What is claimed is:

1. A process for the preparation of Fluvastatin Sodium salt of formula I:

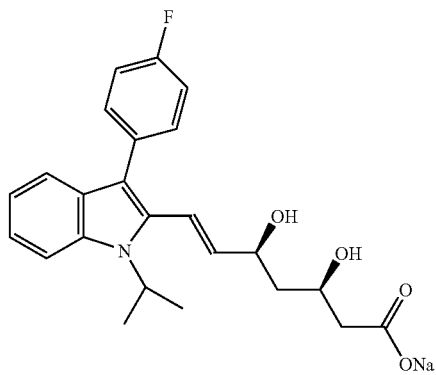

I comprising the reaction of Fluvastatin alkyl ester of formula V:

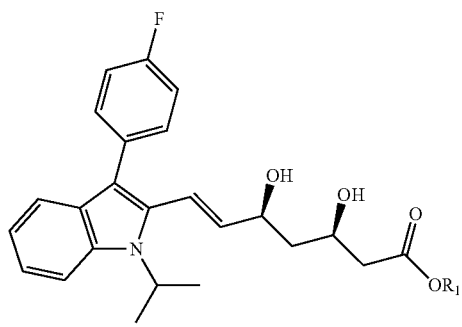

V wherein $R_1$ is t-butyl,
with sodium hydroxide in mixture of a $C_2$-$C_8$ aliphatic alcohol and water, characterized in that less than 1.00 molar amount of sodium hydroxide is used and the volume ratio between said alcohol and water is greater than 5.

2. The process according to claim 1 wherein said alcohol is a $C_2$-$C_5$ aliphatic alcohol.

3. The process according to claim 1 wherein said alcohol is chosen among the group consisting in ethanol, isopropanol, t-butanol, isobutanol and 2-methyl-2-butanol.

4. The process according to claim 1 wherein said alcohol is t-butanol.

5. The process according to claim 1 wherein the volume ratio between said alcohol and water is equal to or greater than 10.

6. The process according to claim 1 wherein the volume ratio between said alcohol and water is between 20 and 1000.

7. The process according to claim 1 wherein the molar amount of sodium hydroxide in respect to the ester is from 0.90 to 0.99.

8. The process according to claim 1 wherein the molar amount of sodium hydroxide in respect to the ester is from 0.95 to 0.98.

9. The process according to claim 1 wherein said process is carried out at a temperature from −10° C. to 50° C.

10. The process according to claim 1 wherein said process is carried out at a temperature from 10° C. to 30° C.

11. The process according to claim 1 further comprising the step of evaporating the mixture of the $C_2$-$C_8$ aliphatic alcohol and water under reduced pressure at the end of the reaction and then adding water.

12. The process according to claim 1 further comprising the step of adding water at the end of the reaction.

13. The process according to claim 1 further comprising the step of extracting the reaction mixture with a solvent immiscible with water.

14. The process according to claim 13 wherein said solvent is chosen among the group consisting in ethers, esters, ketones, aromatic, aliphatic and chlorinated hydrocarbons.

15. The process according to claim 13 wherein said solvent is chosen among the group consisting in t-butyl methyl ether, diethyl ether, diisopropyl ether, methyl ethyl ketone, methyl isobutyl ketone, ethyl acetate, isopropyl acetate, methylene chloride, chloroform and toluene.

16. The process according to claim 13 wherein said solvent is t-butyl methyl ether.

17. The process according to claim 13 further comprising the step of evaporating the aqueous phase and lyophilizing the resulting product.

18. The process according to claim 1 further comprising the step of isolating the product by filtration from the reaction mixture at the end of the reaction.

* * * * *